United States Patent [19]

Owsley et al.

[11] Patent Number: 5,773,588

[45] Date of Patent: Jun. 30, 1998

[54] METHOD FOR PURIFYING SOMATOTROPIN MONOMERS

[75] Inventors: Dennis C. Owsley, St. Louis, Mo.; Suvit Kulvaranon, Kingwood, Tex.

[73] Assignee: Monsanto Company, St. Louis, Mo.

[21] Appl. No.: 566,591

[22] Filed: Dec. 4, 1995

Related U.S. Application Data

[63] Continuation of Ser. No. 246,028, May 19, 1994, abandoned.

[51] Int. Cl.$^6$ .......................................... C07K 1/30
[52] U.S. Cl. ....................... 530/419; 530/412; 530/418; 530/420
[58] Field of Search ................................... 530/412, 418, 530/419, 420

[56] References Cited

U.S. PATENT DOCUMENTS

| | | |
|---|---|---|
| 4,612,367 | 9/1986 | Grinnan et al. . |
| 5,182,369 | 1/1993 | Storrs et al. . |

FOREIGN PATENT DOCUMENTS

| | | |
|---|---|---|
| 0 108 585 | 5/1984 | European Pat. Off. . |
| 0 192 629 | 8/1986 | European Pat. Off. . |
| 0 445 099 | 4/1991 | European Pat. Off. . |
| WO 91/03486 | 3/1991 | WIPO . |

OTHER PUBLICATIONS

H. Choi et al., Isolation and Purification of Human Growth Hormone in Yeast Cells Comprises Suspending Cells in Buffer Solution, Increasing pH, Removing Residue and Purification. Abstract, Derwent Publications Ltd., London, GB.

*Primary Examiner*—Paula K. Hutzell
*Assistant Examiner*—Stephen Gucker
*Attorney, Agent, or Firm*—Gary M. Bond; Arnold, White & Durkee

[57] ABSTRACT

There is provided a method for purifying a refold somatotropin monomer from a mixture of somatotropin monomers and somatotropin oligomers in an aqueous solution having a urea concentration of greater than 3 molar by the addition of an acid to reduce the pH of the solution to below about 7.7 to selectively precipitate the oligomers in the most part.

17 Claims, 1 Drawing Sheet

METHOD FOR PURIFYING SOMATOTROPIN MONOMERS

This is a continuation of application Ser. No. 08/246,028, filed May 19, 1994, now abandoned.

FIELD OF INVENTION

This invention relates to the purification of somatotropin proteins produced by recombinant DNA technology, and more particularly, to the purification and recovery of somatotropin monomers by the separation and removal of somatotropin oligomers, residual host cell proteins and other impurities through a process of selective precipitation.

BACKGROUND OF INVENTION

Recombinant DNA technology has permitted the expression of heterologous proteins in host cells, such as *E. coli* bacteria. In the case of somatotropin, a growth hormone, the protein is sequestered in refractile bodies within the cytoplasm of the host cells. The refractile bodies may be recovered from the host cell culture by disrupting the cell so as to release the refractile bodies, and thereupon collecting the refractile bodies as a solid pellet by differential centrifugation. The refractile bodies are solubilized in an aqueous solution of a suitable chaotropic agent, such as urea or guanidine hydrochloride at an alkaline pH, generally in the range of 10–12. The solubilized protein is subsequently naturized by contact with a mild oxidizing agent to form intramolecular disulfide bonds and refold or return the protein to its biologically active native conformation. Methods for the solubilization and the naturation of somatotropin protein produced by *E. coli* bacteria using recombinant DNA technology are described in U.S. Pat. No. 4,511,502 and U.S. Pat. No. 4,652,630, each of which is incorporated herein by reference.

The refold solution obtained from the naturation step consists of an aqueous solution of somatotropin monomers, dimers and higher oligomers, together with residues and other debris from the host cells. Of these substances, the somatotropin monomer is the desired biologically active agent and must be recovered in a highly purified form suitable for administration by injection to the animal to be treated.

Purification of proteins is a common problem in biotechnology, and several methods to accomplish such purification have been developed.

One such commercially important purification process for purifying and recovering somatotropin monomers from a mixture of somatotropin monomer, somatotropin oligomer and bacterial residue is disclosed in U.S. Pat. No. 5,182,369. In accordance with such process, a solution of somatotropin monomers and somatotropin oligomers is dissolved in water or aqueous urea solution at a pH substantially greater than about 7 to form an aqueous solution of the proteins. The pH of the solution is thereafter reduced to less than about 6.5 with the result that the desired somatotropin oligomers precipitate. The precipitate is removed and the somatotropin is recovered from the solution. In the purification step of the prior art process, as in the present invention, a refold solution is obtained by the solubilization and naturation of refractile bodies in aqueous urea as described in U.S. Pat. No. 4,652,630. The protein dissolved in such refold solution will generally consist of from about 30–60% somatotropin monomers, from about 10–30% somatotropin dimers and higher oligomers, and from about 20–50% residues derived from the *E. coli* including other proteins, membrane fragments, color bodies, endotoxins, pyrogens, nucleic acid, and other debris from the fermentation process. In addition, the refold solution may contain urea at a concentration of from about 1.5 to 6.0 molar. As disclosed in U.S. Pat. No. 4,652,630, a urea concentration of between about 4 and 6 molar is preferred for naturation of bovine somatotropin, while a concentration of between about 2.5 molar and 3.5 molar is preferred for porcine somatotropin.

In accordance with the present invention, it has been found that, to effect a precipitation of the undesired oligomers to provide the purified somatotropin monomer, it is not necessary first to reduce the urea concentration. Hence, the considerable cost which is added by diafiltration or other techniques to remove urea in producing the desired somatotropin monomer is avoided.

SUMMARY OF THE INVENTION

The present invention provides a method for isolating and recovering biologically active somatotropin monomers from a refold solution of somatotropin monomers, somatotropin oligomers and fermentation *E. coli* bacteria residue and having a urea concentration of between about 3.5 molar and preferably about 4 to about 6 molar. The pH of the refold solution will generally be in the range of below about 7.7. The refold aqueous solution generally comprises about 30–60% by weight somatotropin monomer, about 10–30% by weight somatotropin dimer and higher oligomers, and about 20–50% by weight fermentation residues derived from *E. coli* bacteria, including but not limited to, other proteins, cell membrane fragments, color bodies, endotoxins, pyrogens, nucleic acid, etc. The pH of the refold solution which is substantially greater than 8 is reduced to within the range of about 7.7 to about 3.0, preferably 7.5–5.0 with the result that a major portion of the somatotropin oligomer and dissolved residue selectivity precipitates from the solution and a major portion of somatotropin monomer remains in solution. The precipitated material is removed to provide purified somatotropin monomer in the solution.

DESCRIPTION OF DRAWING

The drawing is a typical graph depicting the selective precipitation of somatotropin (BST) monomer, oligomer, and other proteinaceous materials in a refold aqueous solution containing BST monomers, BST oligomers, and other products resulting from a pH reduction of the refold solution by the addition of a suitable acid to the refold solution which has a concentration of urea of 4.5 molarity.

DETAILED DESCRIPTION OF THE INVENTION

Figure 1:
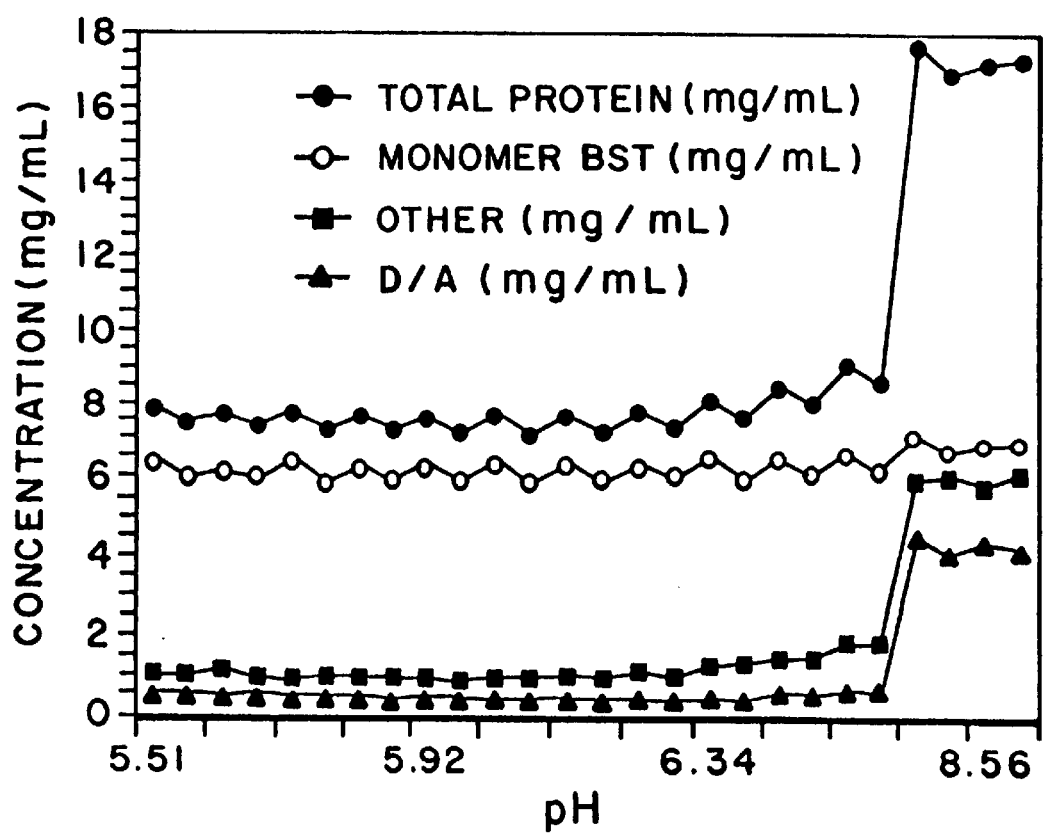

For purposes of the present invention, the following terms should be considered to have the definitions listed below.

The term "somatotropin" is meant to include, but not be limited to, mammalian somatotropins such as human, ovine, porcine and bovine somatotropin and others such as avian somatotropin. In addition to being suitable for the above somatotropin proteins having naturally occurring sequences, the present invention is equally applicable to systems involving analogs and homologs of the naturally occurring protein having somatotropin-like bioactivity. Accordingly, to the extent that such proteins are equivalents for purification purposes, the present invention includes such proteins.

"Heterologous" proteins are proteins which are normally not produced by the host cell. Recombinant DNA technology has permitted the expression of relatively large amounts of heterologous proteins, such as somatotropin from transformed host cells, such as *E. coli*. However, while not fully understood, these foreign proteins are often sequestered in insoluble refractile bodies in the cytoplasm of the host cell.

By "refractile bodies" is meant the inclusion bodies or cytoplasmic aggregates containing, at least in part, the heterologous proteins to be recovered. These aggregates appear as bright spots under a phase contrast microscope.

By "host cell" is meant a microbial cell, such as bacteria and yeast or other suitable cell including animal and plant cells which has been transformed to express the heterologous proteins. Host cells which are contemplated by the present invention are those in which heterologous somatotropin expressed by the cell is sequestered in refractile bodies. An exemplary host cell is *E. coli* K12, strain W311OG pBGH1, which has been transformed to permit expression of bovine or porcine somatotropin.

"Naturation" refers to the folding and oxidation of the heterologous somatotropin protein to its native conformation to ensure biological activity.

"Folding" refers to the formation of the overall conformational shape of the protein sufficient to permit proper oxidation. Folding is accomplished when the amino acid sequence of the protein is free to interact and assume its native secondary and tertiary structure.

"Oxidation" refers to the formation of the intramolecular disulfide bonds in the folded protein to stabilize the native conformation and ensure biological activity.

"Refold Solution" refers to the stock solution obtained as a result of the folding and oxidation in the naturation step.

In the following description and examples, the purification process of the present invention is illustrated with reference to the purification of refold solution obtained by the solubilization and naturation of refractile bodies in aqueous urea as described in U.S. Pat. No. 4,652,630, it being understood that the invention is not limited by the specific details of the process used to produce the refold solution. The naturation step may be conducted at lower pH values and/or with lower concentrations of urea than used in the solubilization step.

In the case of the solubilization and naturation process described in U.S. Pat. No. 4,652,630, the components of a typical refold solution will generally consist of from about 30–60% somatotropin monomers, from about 10–30% somatotropin dimer and higher oligomers, and from about 20–50% residues derived from the *E. coli* bacteria, including but not limited to, proteins, membrane fragments, color bodies, endotoxins, pyrogens and nucleic acids. In addition, the refold solution may contain urea at a concentration of from about 1.5 to 6M depending on the type of somatotropin being oxidized. As disclosed in U.S. Pat. No. 4,652,630, a urea concentration of between about 4 and 6M is preferred for naturation of bovine somatotropin, while a concentration of between about 2.5 and 3.5M is preferred for porcine somatotropin.

It has been found that it is not necessary to reduce the concentration of urea in the refold solution by diafiltration or other steps be taken to substantially reduce the urea concentration of the refold solution.

As described in U.S. Pat. No. 4,652,630, naturation of solubilized somatotropin may be conducted at reduced temperatures such as 4° C. to retard degradation of urea. Temperature is not critical to the precipitation fractionation process of the present invention, however, and the refold solution may be allowed to warm to room temperature if desired. Warmer temperatures in the range of 20°–25° C. may, in fact, offer slightly better oligomer separation.

In one embodiment of the precipitation process of the present invention, the pH of the refold solution is slowly reduced from the high level employed for the naturation step, usually in excess of pH 10, by slowly adding an acid, such as dilute acetic acid or other suitable organic or inorganic acid, with good mixing to avoid pockets of high acid concentration which could alter the pH equilibrium and have a localized effect on the solubility of the protein. The acid is added until a predetermined optimum pH end point value is reached. The optimum pH end point value must be determined individually for each protein system and will depend on variables such as relative proportions of somatotropin monomers and oligomers, the amount of bacterial proteins and contaminants present, and the presence or absence of various chaotropic agents, solvents, salts or solutes which affect the solubility of the proteins. The optimum pH end point value is generally in the range of less than 7.7, and is identified as being within the pH range at which substantially all the bacterial residues and associated contaminants have precipitated, a major portion of the somatotropin oligomer has precipitated and the amount remaining in solution does not exceed maximum levels for acceptable degree of purity of the final product, and a major portion of the somatotropin monomer remains in solution and the amount which has precipitated does not exceed maximum levels for acceptable yields.

In general, process yields and final product purity are inversely related. Higher purities of the final somatotropin monomer product reflecting lower levels of oligomer are obtained at the expense of yield, and the maximum acceptable level of oligomer is established by economical considerations. The somatotropin oligomers act as an inert diluent in the final product, diminishing the effective concentration of the active monomer component and requiring the gross dosage levels administered to the target animal to be increased accordingly. The oligomer is not believed to have any negative activity or to produce any undesirable side effect.

The actual relationship between yield and purity depends to some extent on the upstream conditions employed during the naturation step, and on the quality of feedstock being processed in the precipitation fractionation step. For refold solutions obtained from the solubilization and naturation of refractile bodies in urea as described above, the maximum acceptable level of somatotropin oligomer in the preferred purified somatotropin product has been established as 5% by weight, with the most desirable level being about 2.5% or less. The minimum acceptable yield for somatotropin monomer has been established at 50% with a desired yield of at least 65%. The optimum pH end point to obtain these results must be determined individually for each precipitation purification system, but generally in the range of 4.5 to 7, and most usually about 6 for BST refold solutions when processed as described below.

In a preferred embodiment of the present invention refractile bodies containing BST or PST monomers, oligomers and aggregates along with *E. coli* proteins are received from the fermentation and isolation steps in the recombinant DNA technology as described in each of U.S. Pat. No. 4,511,502 and U.S. Pat. No. 4,652,630. The refractile bodies are dissolved in a concentrated urea solution at a pH of about 11.25–11.3 to provide a refold solution that is finally about 4.5M in urea. The refold step involves oxidizing the sulfhydryl groups in the reduced monomer to oxidized monomer in the native conformation containing the correct disulfide bridges.

In the practice of the invention the refold solution having a concentration of about 4.5M in urea is placed in a container wherein the pH of the refold solution is adjusted to be in the range of 5.8–6.3 with the addition of an acid, preferably a strong mineral acid, such as, for example hydrochloric acid. In the precipitation tank a filter aid, such as diatomaceous earth is added. The resulting precipitate is allowed to settle for one hour or so and is then filtered, preferably through a filter press to a second tank. The filter cake is washed with an aqueous solution of 4.5M urea having a pH of 6.0. The filtrate and wash are combined and the resulting mixture is deionized using a bed resin. Further purification steps may be taken to further improve the purification level of the somatotropin which is ultimately formulated in various ways and administered to the animal to be treated.

The process chemistry involved in the present invention is the neutralization of the proteins dissolved in somatotropin refold solution to below their isoelectric point.

The attached drawing (referred to as a "titration curve" hereinbelow) is a typical plot of concentrations of various protein species in a somatotropin refold solution vs pH when HCl is added to a refold solution. From the prior art, it is well known that most proteins precipitate from solution when their isoelectric point is reached. In the present invention it has been found that in 4.5M or higher concentrations of urea, BST monomer behaves unexpectedly in that it remains in solution throughout the entire pH range shown in the drawing.

With reference now to the accompanying drawing, the refold solution at a pH of 8.5 has a total concentration of protein about 17.5 mg/mL, of which about 7 mg/mL is BST monomer, 4.5 mg/mL dimer aggregate (D/A). The remainder consists of other materials which include residues derived from the E. coli bacteria as described above. When the pH of the refold solution is reduced to about 7.7 or lower by the addition of HCl, virtually all of the BST monomer remains in solution, and most of the BST dimer/aggregate and other materials precipitate. Similar titration curves have been obtained by lowering the pH of refold solutions with hydrobromic acid, sulfuric acid, nitric acid, phosphoric acid, acetic acid and formic acid. The precipitated materials are removed by filtration. The filtrate containing the somatotropin monomer is then treated in a conventional manner to recover the desired protein for further purification and finally into a formulated product suitable for administration to an animal.

The precipitation reaction in the present process is quite pronounced. The effect of process variables, such as BST or PST concentration, temperature and pH on somatotropin yield have been studied, and it has been found, among other things, that the effective pH range is quite wide, ranging from a pH of below about 7.7 to 5.5 and lower. Preferably, the pH at which the precipitation is carried out ranges from 7.5 to 5.8. Concentration of BST may range from about 3 to about 9 grams per liter. Variations in the BST concentration does not appear to have significant effect in the practice of the present invention. Temperature appears to be a variable that has some effect on yields. Good yields are obtained at room temperature. Commonly used acids seem to work equally well in the precipitation of the unwanted proteinaceous substances. The following examples are presented to illustrate but not to restrict the scope of the invention. All percentages are given on a weight to weight basis unless otherwise indicated.

EXAMPLE 1

A quantity of BST somatotropin protein was produced by E. coli bacteria using recombinant DNA technology. The resulting refractile bodies were solubilized in an aqueous 4.5M urea solution at a pH of 11. The solubilized proteins were subsequently naturized by contact with air as an oxidizing agent to form intramolecular disulfide bonds and refold the protein into its native conformation. At 23° C. the refold aqueous solution which contained 82 g of oxidized BST monomer and 35.3 g of other proteins was transferred to a precipitation vessel. The urea concentration of this solution was 4.5M. Diatomaceous earth filter (250 g) was added as a filtration aid. The resulting precipitation batch was stirred at room temperature, and a quantity of 12N HCl was slowly added to reduce the pH of the mixture to 6.0.

EXAMPLE 2

To 92 L of a refold solution in 4.5M urea at room temperature containing 6.18 g/L of BST monomer and 14.49 g/L total protein was added 920 g of Hi-Flo Super Cel filter aid. The solution was at pH 9. The pH of the solution was lowered to pH 6.1 using 12N HCl. The resulting precipitate was stirred for one hour and filtered to yield a solution containing 5.45 g/L monomeric BST (88.2% yield) and 6.84 g/L total protein. The BST dimer/aggregate concentration was 0.57 g/L, while the other proteins measured 0.82 g/L.

EXAMPLE 3

A refold solution (2.0 L) in 4.5M urea at room temperature at a pH of 11.3 was treated with 20 g of Hi-Flo Super-Cel filter aid. The initial solution contained 15.19 g/L total protein and 6.12 g/L of monomeric BST. The pH of the solution was lowered to 6.1 with 0.832N HCl solution. After one hour of stirring, the precipitate was vacuum filtered and washed with 200 mL of 4.5M urea, pH 6.0, to yield 2 L of a solution containing 5.86 g/L monomeric BST (95.7% yield). The filtrate contained 7.37 g total protein. The dimer/aggregate concentration was 0.35 g/L with other proteins at a concentration of 1.16 g/L.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of the patentable novelty which reside in the present invention, including all features which would be treated as equivalents thereof by those skilled in the art to which the invention pertains.

What is claimed is:

1. A process of separating somatotropin monomer from an aqueous solution of somatotropin monomer and somatotropin oligomers having a concentration of urea in excess of 3.5 molar comprising mixing the solution with an acid in an amount to lower the pH below about 7.7 to precipitate selectively the oligomers and then removing the resulting precipitated oligomers.

2. The process of claim 1 wherein the somatotropin is bovine somatotropin.

3. The process of claim 1 wherein the urea concentration of the aqueous solution is about 4–6 molar.

4. The process of claim 1 wherein the pH of the resulting acidified solution is in the range of 7.7–3.0.

5. The process of claim 1 wherein the acid is hydrochloric acid, sulfuric acid, nitric acid, phosphoric acid, acetic acid or formic acid.

6. A process of separating somatotropin monomer selectively from a solution comprised of about 30–60% somatotropin monomer, about 11–30% somatotropin oligomers and about 20–50% residue resulting from a recombinant production of the somatotropins and having a concentration of urea in excess of 3.5 molar comprising mixing the solution with an acid in an amount to lower the pH of the solution below 7.7 to precipitate selectively the oligomers and the residue in the most part and then, removing the resulting precipitated oligomers and residue leaving the somatotropin monomers remaining in the most part in solution.

7. The process of claim 6 wherein the somatotropin is bovine somatotropin.

8. The process of claim 6 wherein the urea concentration of the aqueous solution is about 4–6 molar.

9. The process of claim 6 wherein the pH of the resulting acidified solution is in the range of 7.7–3.0.

10. The process of claim 6 wherein the acid is hydrochloric acid, sulfuric acid, nitric acid, phosphoric acid, acetic acid or formic acid.

11. A process of purifying an aqueous refold solution obtained from naturation of somatotropin protein produced by *E. coli* using recombinant DNA technology and comprised of about 30–60% somatotropin monomers, about 11–30% somatotropin oligomers and about 20–50% residue resulting from the recombinant production of the somatotropins and having a concentration of urea in excess of 3.5 molar and a pH substantially greater than 8, comprising mixing the solution with an acid to lower the pH of the solution below 7.7 to precipitate selectively the oligomers and residue in the most part and then, removing the resulting precipitated oligomers and residue in the most part, thereby leaving the somatotropin monomers in the most part remaining in solution.

12. The process of claim 11 wherein the somatotropin is bovine somatotropin.

13. The process of claim 11 wherein the urea concentration of the aqueous solution is about 4–6 molar.

14. The process of claim 11 wherein the pH of the resulting acidified solution is in the range of 7.7–3.0.

15. The process of claim 11 wherein the acid is hydrochloric acid, sulfuric acid, nitric acid, phosphoric acid, acetic acid or formic acid.

16. The process of claim 11 wherein the pH of the resulting acidified solution is in the range of about 4.5 to 7.

17. The process of claim 11 wherein the pH of the resulting acidified solution is about 6.

* * * * *